United States Patent [19]

Chu

[11] 4,274,982
[45] Jun. 23, 1981

[54] METHOD FOR MAINTAINING PARA-SELECTIVITY OF MODIFIED ZEOLITE CATALYST

[75] Inventor: Chin-Chiun Chu, North Brunswick, N.J.

[73] Assignee: Mobil Oil Corporation, New York, N.Y.

[21] Appl. No.: 84,331

[22] Filed: Oct. 12, 1979

[51] Int. Cl.³ .............................................. B01J 29/28
[52] U.S. Cl. ................................. 252/455 Z; 252/437
[58] Field of Search ........................... 252/455 Z, 437

[56] References Cited

U.S. PATENT DOCUMENTS

| 4,105,541 | 8/1978 | Plank et al. | 252/455 Z |
| 4,137,195 | 1/1979 | Chu | 252/455 Z |
| 4,139,600 | 2/1979 | Rollmann et al. | 252/455 Z |

*Primary Examiner*—Carl F. Dees
*Attorney, Agent, or Firm*—Charles A. Huggett; Charles J. Speciale; Ronald J. Cier

[57] ABSTRACT

A method for prolonging the useful life of para-selective modified zeolite catalysts, said zeolites having a silica to alumina mole ratio of at least about 12, a constraint index of about 1–12 and having been modified by the addition thereto of a minor proportion of a difficultly reducible oxide. The selective catalyst is maintained at temperatures of at least about 50° C. or, alternatively, in an atmosphere substantially free of moisture.

11 Claims, No Drawings

METHOD FOR MAINTAINING PARA-SELECTIVITY OF MODIFIED ZEOLITE CATALYST

BACKGROUND OF THE INVENTION

1. Field of the Invention

This invention pertains to modified zeolite catalysts useful for selective alkylation of aromatic molecules and selective disproportionation of mono- and di-alkylaromatics. It is particularly directed to maintenance of the high para-selectivity of such modified catalysts.

2. Description of the Prior Art

Modification of certain types of crystalline zeolite catalysts by deposition of phosphorus and magnesium thereon is known to cause a desirable increase in the selectivity to the para isomer when the modified catalyst is utilized to promote alkylation of aromatic molecules and/or disproportionation reactions of mono- and di-alkylaromatic molecules. Such catalysts are disclosed in U.S. Pat. Nos. 4,011,276 to C. Chu and 4,128,592 to W. W. Kaeding, for example.

It has been found, however, that the desirable para selectivity characteristics of these catalysts rapidly deteriorate on scale-up of the reaction from laboratory-scale reactors to commercially viable large-scale reactors. While the overall activity of the modified catalysts remains high (i.e. the overall alkylation or disproportionation activity), the selectivity to the expected para isomers drops off at an alarming rate. In some cases this "aging" of the selective characteristics of these catalyst has been reported to be as high as 20% or more per day in the reactor.

SUMMARY OF THE INVENTION

In accordance with the present invention, it has been discovered that the advantageous para selectivity of modified zeolite catalysts may be maintained at desirably high levels by keeping the catalyst at elevated temperatures after activation or, alternatively, by storing and/or using the activated catalyst at lower temperatures in a substantially water-free atmosphere. The foregoing modified zeolite catalysts comprise crystalline zeolites having a silica to alumina mole ratio of at least about 12 and a constraint index within the approximate range of 1 to 12, which zeolite has been modified by the addition thereto of a minor proportion of one or more difficulty reducible oxides, such as, for example, a minor proportion of an oxide of phosphorus and a minor proportion of an oxide of magnesium.

The present method comprises maintaining the activated oxide-modified catalyst at temperatures of about 50° C. or higher during use and also prior to use during the initial reactor start-up period following activation or re-cycling of the catalyst. During storage at ambient temperature and when in the reactor at temperatures of below about 50° C., the activated catalyst is maintained in an atmosphere which is substantially free of moisture.

DESCRIPTION OF SPECIFIC EMBODIMENTS

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred in some applications to use zeolites having higher silica/alumina ratios of at least about 30. In addition, zeolites as otherwise characterized herein but which are substantially free of aluminum, i.e. having silica to alumina mole ratios of 1,600 and higher, are found to be useful and even preferable in some instances. Such "high silica" zeolites are intended to be included within this description. The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted to between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10% to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, and other similar materials.

ZSM-5 is described in greater detail in U.S. Pat. Nos. 3,702,886 and 3,941,871. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

ZSM-38 is more particularly described in U.S. Pat. No. 4,046,859. The description of that catalyst, and particularly the specified X-ray diffraction pattern thereof, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35 and ZSM-38, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The crystals of zeolite in a form substantially free of alkali metal, i.e. containing less than about 1.5 weight percent alkali metal and preferably having at least a portion of the original cations associated therewith replaced by hydrogen, are then modified by depositing thereon a minor amount of one or more difficultly reducible oxides, thereby enhancing the para-selectivity of the zeolite in aromatic alkylation and/or disproportion reactions. Representative elements, the oxides of which may be beneficially combined with the zeolites, include antimony, arsenic, boron, calcium, magnesium, nickel, phosphorus, silicon, uranium and zinc, among others. The oxides of such elements may be utilized individually or in combination with the oxides of other elements. One particularly preferred embodiment is with respect to zeolites of enhanced para-selectivity due to modification with oxides of magnesium and phosphorus, and especially ZSM-5 which has been so modified.

Modification may be accomplished by contacting the zeolite with a compound of the desired element and then heating the compound-impregnated zeolite to convert the desired element to its oxide form. For instance, the zeolite may be contacted with a phosphorus compound. Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=S$, $RPO_2$, $PRS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2RSP(SR)_2$, and $(RO)_2POP(OR)_2$, where R is an alkyl or aryl, such as a phenyl radical, and X is hydrogen, R, or a halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphonates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites and esters thereof such as the monopropyl ester, alkyl dialkylphosphinites, $(RO)PR_2$, and dialkyl alkylphosphinite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain from one to four carbon atoms.

Other suitable phosphorus-containing compounds include the phosphorus halides, such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, and dialkyl phosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

Preferred phosphorus-containing compounds include diphenyl phosphine chloride, trimethylphosphite, diammonium hydrogen phosphate, ammonium dihydrogen phosphate, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid or a solid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as octane may be employed. The phosphorus-containing compound may be used without a solvent, i.e. as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite, such as air or nitrogen, or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen—for example, in air. Heating can be at a temperature of about 150° C. However, higher temperatures, e.g., up to about 500° C., are preferred. Heating is generally carried out for 3–5 hours but may be extended to 24 hours or longer. While heating temperatures above about 500° C. can be employed, they are generally not necessary. At temperatures of about 1000° C. the crystal structure of the zeolite tends to deteriorate.

The amount of phosphorus incorporated with the zeolite should be at least about 0.25 percent by weight. However, it is preferred that the amount of phosphorus in the zeolite be at least about 1 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.5 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated within the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction with the treating compound, and the amount and type of binder incorporated with the zeolite.

The zeolite, containing phosphorus oxide, is then preferably further combined with magnesium oxide by contact with a suitable compound of magnesium. Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Reaction of the zeolite with the treating magnesium compound is effected by contacting the zeolite with such compound. Where the treating compound is a liquid or solid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. as a neat liquid. Where the treating compound is in the gaseous phase, it can be used by itself or in admixture with a gaseous diluent relatively inert to the treating compound and the zeolite (such as helium or nitrogen) or with an organic solvent such as octane or toluene.

Heating of the magnesium compound impregnated catalyst subsequent to preparation and prior to use is preferred. The heating can be carried out in the presence of oxygen—for example, in air. Heating can be at a temperature of about 150° C. However, higher temperatures, e.g. up to about 500° C., are preferred. Heating is generally carried out for 1–5 hours but may be extended to 24 hours or longer. While heating temperatures above about 500° C. may be employed, they are generally not necessary. At temperatures of about 1000° C. the crystal structure of the zeolite tends to deteriorate. After heating in air at elevated temperatures, the oxide form of magnesium is present.

The amount of magnesium oxide incorporated in the calcined phosphorus oxide-containing zeolite should be at least about 0.25 percent by weight. However, it is preferred that the amount of magnesium oxide in the zeolite be at least about 1 percent by weight, particularly when the same is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 0.5 and about 15 percent by weight.

The amount of magnesium oxide incorporated with the zeolite by reaction with the treating solution and subsequent calcination in air will depend on several factors. One of these is the reaction time, i.e. the time that the zeolite and the magnesium-containing source are maintained in contact with each other. With greater reaction times, all other factors being equal, a greater amount of magnesium oxide is incorporated with the zeolite. Other factors upon which the amount of magnesium oxide incorporated with the zeolite is dependent include reaction temperature, concentration of the treating compound in the reaction mixture, the degree to which the zeolite has been dried prior to reaction with the treating compound, the conditions of drying of the zeolite after reaction of the zeolite with the magnesium compound and the amount and type of binder incorporated with the zeolite.

The above-described Mg-P modified zeolite catalyst is useful in promoting alkylation reactions and in disproportionation of alkylated aromatics (e.g. toluene, xylene, etc) and maximizing the yield of the para isomer of the resulting dialkylbenzene compounds. Examples of these reactions and suitable conditions therefor are disclosed in U.S. Pat. Nos. 4,011,276 and 4,128,592, both of which are incorporated herein by reference.

It has been found that these catalysts, when placed in a large-scale reactor, frequently lose a significant proportion of their desirable para selectivity during normal start-up and stabilization periods of the reactor. While overall activity of the catalyst would remain good, this undesirable deselectivation has been known to proceed at the rate of 20% and more per day.

By practice of the present invention, it has been discovered that such deselectivation of the modified, para-selective catalyst can be prevented and the useful life of the catalyst significantly extended. This very desirable result is accomplished by maintaining the activated catalyst at a temperature of approximately 50° C. or higher when it is in the reactor. At temperatures of less than about 50° C. it is important to avoid contact of the catalyst with moisture, therefore at lower temperatures the catalyst should be contained within an atmosphere which is substantially free of water. This may be accomplished by continuously passing a stream of dried gas (e.g. air or $N_2$ from which substantially all of the moisture vapor has been removed) across the catalyst, or by storage of the catalyst in sealed, moisture-impervious containers.

The process of the present invention and the significant benefit to be gained by the practice thereof will be illustrated with the aid of the following examples. These examples are presented only for purposes of illustration of the concept disclosed herein and should not be construed as presenting undue limitations thereon.

EXAMPLE 1

Preparation of Mg-P-ZSM-5

To a solution of 3.90 kg of $(NH_4)_2.HPO_4$ in 16.2 kg of $H_2O$ was added 9.75 kg of steamed $NH_4$-ZSM-5. The mixture was allowed to stand at room temperature for 16 hours then filtered, dried overnight, and calcined at 500° C. (930° F.) in air for 3 hours. A portion of this P-modified ZSM-5 (1.36 kg) was added to a solution of 3.4 kg Mg(OA$_c$)$_2$ in 2.7 kg H$_2$O and allowed to stand at room temperature for 21.5 hours. The zeolite was then drained, dried, and then calcined at 500° C. for 1 hour. Analysis showed the modified catalyst to contain 2.67 wt.% phosphorus and 7.1 wt.% magnesium.

EXAMPLE 2

Ethylation of toluene in the presence of the Mg-P-ZSM-5 catalyst of Example 1 was carried as follows. In all cases the reactor held 8.0 grams of the catalyst. The reaction was run at 425° C. and 100 psig with a WHSV (feed rate) of toluene/ethylene/hydrogen of 29.8/1.15/0.25, respectively.

Procedure for Testing:

(a) The freshly loaded catalyst was calcined at 500° C. with 500 cc of air per minute overnight.

(b) Ethylation of toluene was run under the conditions described above for 2 hours.

(c) The catalyst was then regenerated at 500° C. with 500 cc of air per minute for 5 hours.

(d) The catalyst bed temperature was then cooled to the desired temperature (i.e.: 500° C., 400° C., 300° C., 200° C., 110° C., 90° C., 50° C. or 30° C.) and the above-mentioned stream of air at 500 cc/min was first passed through a water tower to saturate it with water vapor and then passed across the catalyst bed at the desired temperature for 14 hours. This treatment resulted in carrying 10 grams of water vapor into the catalyst bed along with the air stream.

(e) The air stream was discontinued and changed to a N$_2$ stream and the catalyst bed was heated to 400° C. for 1 hour.

(f) Ethylation of toluene was then run under the conditions described above for an additional 2 hours to check the effects of the H$_2$O treatment.

(g) The testing then proceeded from Step (c) above, except at the next lower temperature, and repeated until the run at 30° C. was completed.

(h) The catalyst was then calcined again at 500° C. as in Step (a) and the ethylation reaction repeated. The results are shown in Table I.

TABLE I

EFFECTS OF WATER SATURATED AIR ON PARA-SELECTIVITY OF Mg-P-ZSM-5

| Catalyst Treatment | Ethylation of Toluene | |
|---|---|---|
| | Tol.Conv.* | PET/ET** |
| Fresh cat. calcined 500° C. with 500cc/min air 14 hrs | 9.7% | 94.4% |
| Calcined 5 hrs at 500° C. with 500cc/min air Then air through H$_2$O tower for 14 hrs at 500 C. | 9.8% | 93.9% |
| Calcined 5 hrs at 500° with 500cc/min air Then air through H$_2$O tower for 14 hrs at 400° C. | 9.3% | 94.9% |
| Calcined 5 hrs at 500° C. with 500cc/min air Then air through H$_2$O tower for 14 hrs at 300° C. | 10.2% | 94.4% |
| Calcined 5 hrs at 500° C. with 500cc/min air Then air through H$_2$O tower for 14 hrs at 200° C. | 9.3% | 94.1% |
| Calcined 5 hrs at 500° C. with 500cc/min air Then air through H$_2$O tower for 14 hrs at 110° C. | 9.5% | 95.1% |
| Calcined 5 hrs at 500° C. with 500cc/min air then air through H$_2$O tower for 14 hrs at 90° C. | 8.7% | 96.0% |
| Calcined 5 hrs at 500° C. with 500cc/min air Then air through H$_2$O tower for 14 hrs at 50° C. | 9.9% | 96.6% |
| Calcined 14 hrs at 500° C. with 500cc/min air Then air through H$_2$O tower for 14 hrs at 30° C. | 9.9% | 61.4% |
| Calcined 14 hrs at 500° C. with 500cc/min air | 10.1% | 65.4% |

NOTES:
*% of toluene feed converted to ethyltoluene.
**% para-ethyltoluene in ethyltoluene product.

The fresh catalyst resulted in a toluene conversion rate of 9.7% (77.6% of theoretical conversion) with a selectivity of the para isomer of 94.4%. There was no significant change in conversion rate and selectivity as a result of contacting the catalyst with moisture at temperatures of as low as 50° C. However, when the catalyst was brought into contact with moist air at 30° C. (ambient temperature) dramatic deselectivation took place, with the selectively to para isomer dropping to 61.4%. Re-calcining of the deselectivated catalyst did not restore its selectivity.

EXAMPLE 3

Selective toluene disproportionation (STDP) was tested as follows. A reactor containing 8.0 grams of the catalyst of Example 1 was heated to 500° C. A feed stream of toluene was passed across the catalyst at atmospheric pressure and WHSV of 3.5. The procedure was essentially the same as given in Example 2 except that the catalyst treatment was first with wet air at 500° C., then with wet N$_2$ at ambient temperature (about 25° C.) for 2 hours, and finally with wet N$_2$ at ambient temperature for 14 hours. The results are summarized in Table II.

TABLE II

DISPROPORTIONATION OF TOLUENE AT ATMOSPHERIC PRESSURE

| | Tol. Conv.* | PX/XYL** |
|---|---|---|
| Fresh Catalyst | 2.2% | 82.0% |
| Calcined 500° C. overnight after treatment with wet air at 500° C. for 2 hrs | 2.3% | 85.3% |
| Calcined 500° C. overnight after treatment with wet N$_2$ at ambient temperature for 2 hrs | 2.0% | 68.6% |
| Calcined 500° C. overnight Calcined 500° C. 7½ hrs after treatment with wet N$_2$ at ambient temperature for 14 hrs | 2.1% 2.2% | 70.8% 38.3% |

NOTES:
*% of toluene feed converted to xylene.
**% para isomer in xylene product.

As can be seen, wet air treatment of the catalyst at 500° C. improved selectivity to the para isomer slightly. However, significant deselectivation of the catalyst occurred after treatment with wet $N_2$ at ambient temperature for only 2 hours. Recalcining of the catalyst at 500° C. overnight failed to bring about significant improvement in selectivity. Longer exposure of the catalyst to moist $N_2$ at ambient temperature resulted in further drastic deselectivation.

EXAMPLE 4

Preparation of Mg-ZSM-5

A sample of HZSM-5 zeolite was precalcined and made into 8-14 mesh size. An 18.0 g portion was added to a solution of 30.0 g $Mg(OAc)_2.4H_2O$ in 30 ml of $H_2O$ at 90° C. The mixture was maintained at 90° C. (plus/minus 5° C.) for 2 hours. After removal of the magnesium acetate solution, the Mg-impregnated catalyst was dried at approximately 90° C. in an oven and then calcined at 500° C. for 2 hours. Magnesium content of the Mg.ZSM-5 was measured to be 6.5 wt.%.

EXAMPLE 5

A 4.0 g sample of the Mg-ZSM-5 catalyst of Example 4 was placed in a flow reactor and tested for para-selectivity in selective toluene disproportionation (STDP) and ethylation of toluene.

STDP was carried out by passing toluene over the Mg.ZSM-5 catalyst at 500° C. and feed WHSV of 3.5 $hr^{-1}$. Toluene conversion was 4.3% and 53.4% of the xylene produced was the para isomer.

Ethylation of toluene was accomplished by passing a feed stream of ethylene and toluene over the catalyst (WHSV of toluene was 7 and that of ethylene was 0.5) at 400° C. The conversion of toluene was 20.3% and the yield of para-ethyltoluene in the total ethyltoluene produced was 86.4%.

EXAMPLE 6

The Mg-ZSM-5 catalyst in Example 5 was calcined in air at 500° C. for 16 hours. After it was cooled to ambient temperature, a stream of nitrogen was passed through a water reservoir and then into the catalyst bed for 2 hours at ambient temperature. The catalyst was thereafter dried in situ at 100° C. for 1 hour with the aid of a stream of (dry) $N_2$ and calcined at 500° C. for 2 hour. STDP and ethylation of toluene were then tested as recited in Example 5. STDP gave a toluene conversion of 5.3% with 38.1% para isomer in the xylene product. Ethylation of toluene resulted in a toluene conversion rate of 12.7% with 71.8% of the ethyltoluene product being the para isomer.

EXAMPLE 7

A fresh 4.0 g sample of the Mg-ZSM-5 catalyst of Example 4 was placed in the reactor and maintained at 50° C. while a stream of wet $N_2$ was passed over the catalyst bed for 2 hours as in Example 6. The catalyst was then dried at 100° C. for 1 hour and calcined at 500° C. for an additional hour, both in a nitrogen atmosphere.

STDP and ethylation of toluene were carried out in the same manner as Examples 5 and 6. STDP gave a toluene conversion rate of 5.7% with a xylene product having 65.9% of the para isomer. Ethylation of toluene yielded 90.1% para-ethyltoluene in the ethyltoluene product at a toluene conversion of 20.0%.

The foregoing examples demonstrate that, by maintaining the catalyst at temperatures of 50° C. or higher, or alternatively in a moisture-free atmosphere, the useful life of the modified catalysts can be advantageously extended. At temperatures of below about 50° C., contact of the catalyst with water vapor is shown to have a profound adverse effect on the selectivity to the desired para isomer. This undesirable deselectivation is shown to be irreversible by conventional methods of reactivating spent zeolite catalysts.

It is to be understood that the foregoing description is intended to be merely illustrative of certain specific embodiments of the present invention. Many variations thereon may be made by those skilled in the art, within the scope of the following claims, without departing from the spirit of the disclosed invention.

What is claimed is:

1. A method for prolonging the useful life of para-selective modified zeolite catalysts comprising maintaining said selective zeolite catalyst at temperatures of at least 50° C., said zeolite being characterized by a silica to alumina mole ratio of at least about 12 and a constraint index within the approximate range of 1 to 12, and which zeolite has been modified by the addition thereto of at least 0.25 percent by weight of one or more difficulty reducible oxides.

2. A method as described in claim 1 wherein said para-selective zeolite comprises the catalyst bed of a reactor utilized for the alkylation or disproportionation of aromatic compounds to yield dialkylaromatic compounds.

3. A method as described in claim 1 wherein said zeolite is modified by the addition thereto of magnesium oxide in an amount of at least 0.25 percent by weight.

4. A method as described in claim 1 wherein said zeolite is modified by the addition thereto of both magnesium oxide and phosphorus oxide, each in an amount of at least 0.25 percent by weight.

5. A method as described in claim 1, 2, 3 or 4 wherein said zeolite is ZSM-5.

6. A method as described in claim 1, 2, 3, or 4 wherein said zeolite is combined with a binder therefor.

7. A method for prolonging the useful life of para-selective modified zeolite catalysts comprising maintaining said selective zeolite in an atmosphere substantially free of moisture, said zeolite being characterized by a silica to alumina mole ratio of at least about 12 and a constraint index within the approximate range of 1 to 12, which zeolite has been modified by the addition thereto at least 0.25 percent by weight of one or more difficultly reducible oxides.

8. A method as described in claim 7 wherein said zeolite is modified by the addition thereto of magnesium oxide in an amount of at least 0.25 percent by weight.

9. A method as described in claim 7 wherein said zeolite is modified by the addition thereto of both magnesium oxide and phosphorus oxide, each in an amount of at least 0.25 percent by weight.

10. A method as described in claim 7, 8 or 9 wherein said zeolite is ZSM-5.

11. A method as described in claim 7, 8 or 9 wherein said zeolite is combined with a binder therefor.

* * * * *